United States Patent [19]

Reddy et al.

[11] Patent Number: 4,932,956
[45] Date of Patent: Jun. 12, 1990

[54] PROSTATE BALLOON DILATOR

[75] Inventors: Pratap K. Reddy, Bloomington; Michael A. Mikulich, Shakopee; David W. Clark, New Hope, all of Minn.

[73] Assignee: American Medical Systems, Inc., Minnetonka, Minn.

[21] Appl. No.: 347,354

[22] Filed: May 4, 1989

Related U.S. Application Data

[63] Continuation-in-part of Ser. No. 192,432, May 10, 1988.

[51] Int. Cl.[5] ..................... A61M 29/00; A61M 25/10
[52] U.S. Cl. ..................... 606/192; 604/101; 604/54
[58] Field of Search ..................... 604/96, 101, 54, 48, 604/49; 606/191, 192

[56] References Cited

U.S. PATENT DOCUMENTS

| | | | |
|---|---|---|---|
| 2,936,760 | 5/1960 | Gants | 604/101 |
| 4,456,011 | 6/1984 | Warnecke | |
| 4,573,966 | 3/1986 | Weikl et al. | 604/53 |
| 4,610,662 | 9/1986 | Weikl et al. | 604/53 |
| 4,636,195 | 1/1987 | Wolinsky | 604/53 |
| 4,637,396 | 1/1987 | Cook | |
| 4,660,560 | 4/1987 | Klein | |
| 4,702,252 | 10/1987 | Brooks et al. | |
| 4,705,502 | 11/1987 | Patel | 604/49 |

OTHER PUBLICATIONS

Deisting, W., Urol. Internation, 2, 158–171 (1956).

Primary Examiner—Stephen C. Pellegrino
Attorney, Agent, or Firm—Peter C. Richardson; Lawrence C. Akers; Mark Dryer

[57] ABSTRACT

An apparatus for dilation of the prostate urethra which comprises a urinary catheter for insertion in the prostate urethra, dilation means comprising a balloon having an integral protuberance, said means being mounted on the proximal section of the catheter and in communication with the interior of the catheter, location means mounted axially on the catheter at a distance from the dilation means such that the location means is at the bulbous urethra when the dilation means is at the prostate urethra, and activating means for activating said dilation means and said location means. A method for the treatment of benign prostatic hyperplasia comprises inserting a catheter having dilation means and location means and removing the catheter after dilation.

17 Claims, 3 Drawing Sheets

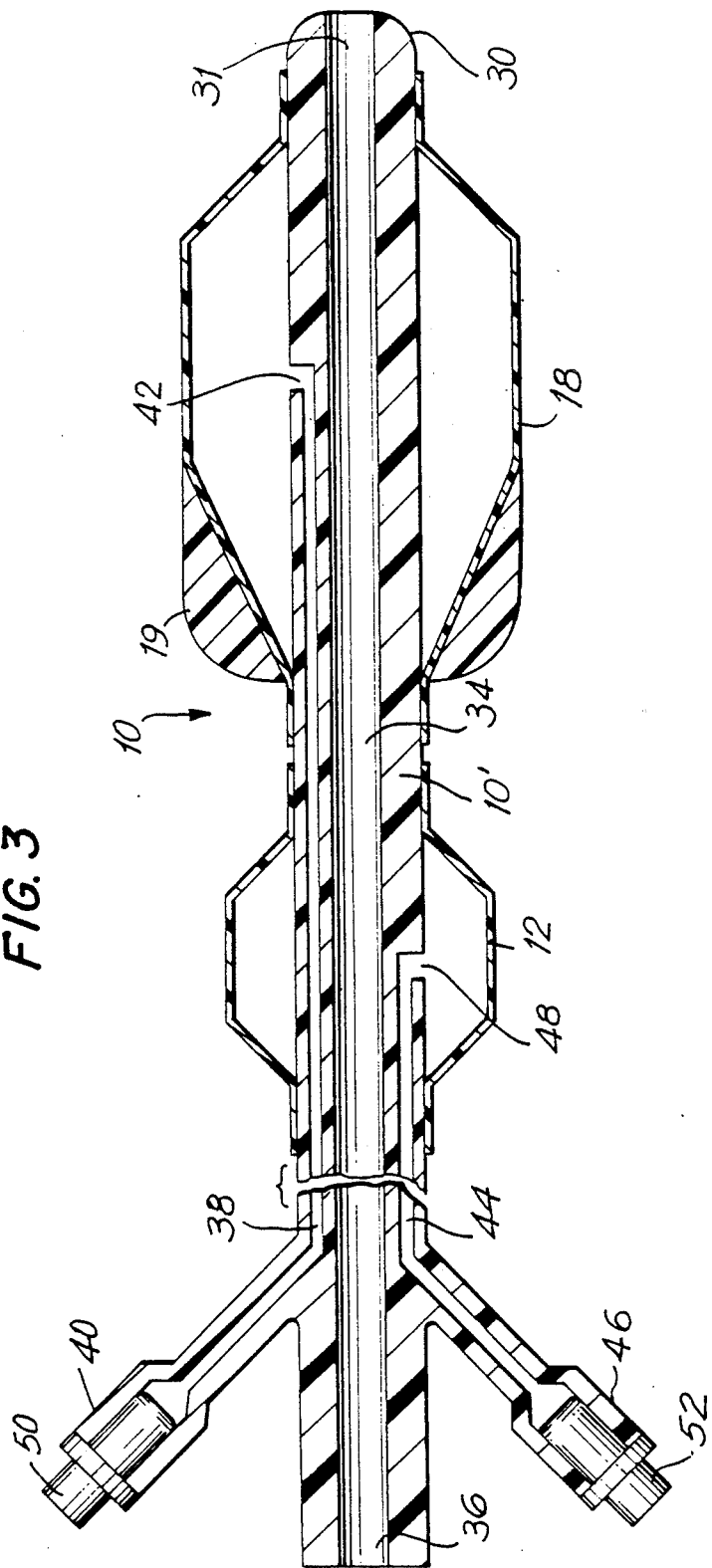

PROSTATE BALLOON DILATOR

CROSS-REFERENCE TO RELATED APPLICATION

This is a continuation-in-part of patent application Ser. No. 192,432 filed May 10, 1988.

BACKGROUND OF THE INVENTION

The invention relates to a catheter having inflatable means for dilation of the prostate urethra, and to a method for the treatment of benign prostatic hyperplasia.

Balloon catheters are widely used for dilation of undesirable tissue in body vessels. For instance, U.S. Pat. No. 4,636,195 discloses removal of constrictions caused by deposition of plaque in arteries by a balloon catheter. The disclosed catheter has two smaller ring balloons spaced around a central dilation balloon. The smaller ring balloons provide a chamber around a body of plaque, and help to hold the catheter body in place. Other multiple balloon catheters are disclosed in U.S. Pat. Nos. 4,573,966 and 4,610,662. The two balloons of these catheters are placed in a vascular passageway to seal off a constricted area, and dissolving fluid is supplied to the enclosed area to dissolve the constrictive tissue.

Treatment of obstructive tissue in the prostate urethra with a balloon catheter is disclosed in U.S. Pat. No. 4,660,560 which describes a catheter having a Foley balloon for anchoring the catheter by inflation within the bladder, and an annular balloon for dilation of the prostate urethra. Proper location of the annular balloon is attained by introducing a cystoscope into the prostate urethra. The operation of the cystoscope to determine the location of the prostate urethra with respect to the bladder neck is cumbersome, and is avoided by the invention as described below.

In Application Ser. No. 192,432 there is described and claimed an apparatus for dilation of the prostate urethra, which apparatus comprises an impervious urinary catheter for insertion in the prostate urethra, said catheter having a proximal section and a distal section: dilation means mounted on said proximal section of the catheter; location means mounted on the catheter at a distance from the dilation means such that the location means is positioned at the bulbous urethra distal from the external sphincter to hold the catheter in place when the dilation means is positioned at the prostate urethra; and activating means located at said distal section of the catheter for activating said dilation means and said location means.

As used herein, the term impervious means both that the material from which the catheter is made is impervious and also that the catheter tube is impervious in that the tubular wall does not have any openings along its length.

In a preferred embodiment of the above invention, the dilation means is a dilation balloon and the location means is a location balloon.

The dilation balloon is preferably made of a limited distensible material such that the balloon can not expand from its initial deflation diameter to substantially beyond a predetermined diameter regardless of the internal pressure applied to the balloon.

Application Ser. No. 192,432 also describes and claims a method for the treatment of benign prostatic hyperplasia which comprises inserting into a prostate urethra an impervious urinary catheter having dilation means for dilating the prostate urethra and location means for location of the dilation means at the prostate urethra, locating and fixing said location means, placing and dilating said dilation means and thereby dilating the prostate urethra with said dilation means to alleviate obstruction of the prostate urethra resulting from benign prostatic hyperplasia, deactivating said dilation means and location means, and removing said catheter from said prostate urethra.

In said method the dilation means is preferably a dilation balloon and the location means is preferably a location balloon.

To facilitate performance of the method the location balloon is axially mounted on said catheter at a distance from said dilation balloon such that the location balloon is positioned at the bulbous urethra distal from the external sphincter to hold the catheter in place when the dilation balloon is positioned at the prostate urethra, and said location balloon on inflation is sized to fit in the bulbous urethra.

A convenient way to properly place the catheter is by rectal palpation wherein the doctor feels the bulbous urethra by rectal palpation and locates the location balloon therein as hereinafter described.

It has now been found that palpation is facilitated when the distal end of the dilation balloon is provided with an integral protuberance which makes it slightly stiffer and thicker than the remainder of the balloon whereby palpation is enhanced when the protuberance is placed at the apex of the prostate. This structure facilitates correct placement of the dilation balloon in the prostate urethra and the location balloon in the bulbous urethra.

SUMMARY OF THE INVENTION

Accordingly, the present invention provides an apparatus for dilation of the prostate urethra comprising: (i) an impervious urinary catheter for insertion in the prostate urethra, said catheter having a proximal section and a distal secton; (ii) a dilation balloon mounted on said proximal section of the catheter, said dilation balloon having a proximal end and a distal end wherein the distal end has an integral protuberance which makes the balloon wall at said distal end thicker and stiffer than the remainder of the balloon wall; (iii) a location balloon mounted on the catheter at a distance from the dilation balloon such that the location balloon is positioned at the bulbous urethra distal from the external sphincter to hold the catheter in place when the dilation balloon is positioned at the prostate urethra; and (iv) activating means located at said distal section of the catheter for activating said dilation balloon and said location balloon.

Preferably the dilation balloon and location balloon are made from a biocompatible material such as silicone elastomer, polyvinylchloride, polyester, natural or synthetic rubber, or polyurethane.

In a preferred embodiment the dilation balloon is made from a multi-layer material, particularly a multi-layer limited distensible material as hereinafter described. A particularly preferred multi-layer material comprises an outer layer of silicone and an inner layer of polyester. An outer layer of silicone is particularly preferred because it increases patient comfort by providing a smooth outer surface for the dilation balloon when it is deflated.

In a particularly preferred embodiment a suitable lubricant, for example a fluorosilicone oil, may be placed between the layers, especially the outer smooth silicone layer and its adjacent inner layer, to ensure smooth relative sliding motion of each layer with respect to the adjacent layer.

The present invention also provides a method for the treatment of benign prostatic hyperplasia in a patient which comprises: inserting into the patient's prostate urethra a hollow, impervious, urinary catheter having a dilation balloon for dilating the prostate urethra and a location balloon for locating the dilation balloon at the prostate urethra, said dilation balloon having a proximal end and a distal end wherein the distal end has an integral protuberance which makes the balloon wall at said distal end thicker and stiffer than the remainder of the balloon wall, and said location balloon being axially mounted on said catheter at a distance from said dilation balloon such that the dilation balloon is positioned at the prostate urethra when the location balloon is positioned at the bulbous urethra distal from the external sphincter, and said location balloon on inflation being sized to fit in the bulbous urethra; placing said dilation balloon at the prostate urethra by palpating said protuberance at the apex of the prostate while locating and fixing said location balloon at the bulbous urethra; dilating the prostate urethra with said dilation balloon to alleviate obstruction of the prostate urethra resulting from benign prostatic hyperplasia; deflating said dilation balloon and location balloon; and removing said catheter from said prostate urethra.

Removal of the catheter is facilitated with minimal distress to the patient when the dilation balloon is made of a multi-layer material, especially wherein the outer layer is silicone and the inner layer is, for example, a polyester. In such an embodiment the outer layer when deflated, because of its smooth and elastic character, bends over and folds in any wings and spikes in the deflated inner layer to provide a smooth outer surface of acceptable small diameter for easy withdrawal.

Smooth deflation is further enhanced by placing a lubricant between the layers of the multi-layer material to provide smooth relative sliding motion of the layers with respect to each other.

BRIEF DESCRIPTION OF THE DRAWINGS

A preferred embodiment of the invention is illustrated in the accompanying drawings, in which:

FIG. 3 is a cross-sectional view of the device of FIG. 1 showing the balloons in inflated condition.

DETAILED DESCRIPTION OF THE INVENTION

Figure 1:
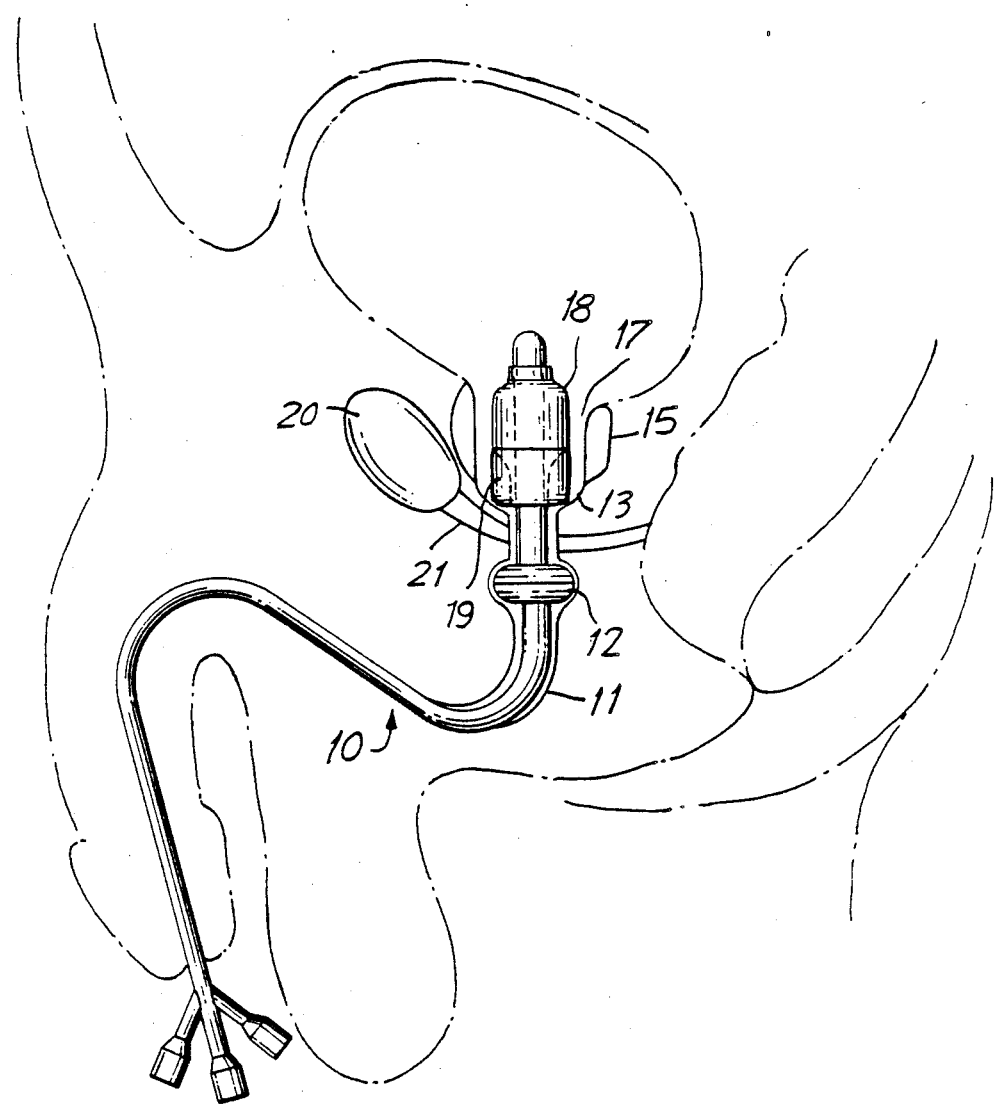
FIG. 1 illustrates a dual balloon catheter according to the invention as it is inserted in the male urethra, showing the balloons in inflated condition.

The embodiment illustrated in FIG. 1 comprises a dual balloon catheter 10 positioned within the male urethra 11. Inflatable location balloon 12 located at the bulbous urethra anchors the device 10 in place and secures it against significant movement in the longitudinal directions, particularly in the direction of the bladder. Inflatable dilation balloon 18 is located at the prostate urethra 13 near the prostate 15 and extends into the bladder neck 17. An integral protuberance 19 is located at the distal end of the dilation balloon 18. This protuberance makes the balloon wall at said distal end thicker and stiffer than the remainder of the balloon wall and thus enhances palpability permitting more reliable placement of the dilation balloon at the apex of the prostate. FIG. 1 shows the location of the male urethra relative to the pubic bone 20 and the urogenital diaphragm (or pelvic floor) 21.

Figure 2:
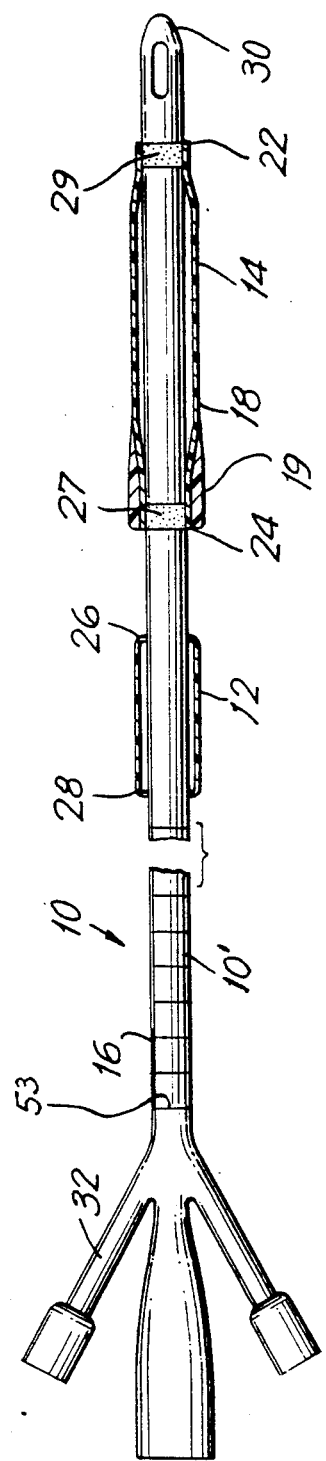
FIG. 2 is a fragmentary sectional view of the device of FIG. 1.

FIG. 2 shows the device 10 comprising catheter tube 10' having proximal section 14 for location toward the center of the body on proper insertion of the device 10 in the body, and distal section 16 for location away from the center of the body on proper insertion of the device 10 in the body.

The catheter tube 10' is formed of a material which is flexible enough to follow the bends in the urethra on insertion of the device 10. The material should be rigid enough, however, to allow the device 10 to pass over any obstructions within the urethra on insertion of the device 10. The catheter tube is composed of or covered by a biocompatible material to avoid irritations and complications in the urethra. Suitable biocompatible materials which can be made into tubing of suitable flexibility and rigidity are silicone, polyester, polyvinylchloride, and polyurethane.

Mounted on the proximal section 14 is axial dilation balloon 18 and axial location balloon 12. Dilation balloon 18 is in communication with the interior of catheter tube 10', as described in more detail with reference to FIG. 3. Dilation balloon 18 has an integral protuberance 19 at its distal end 24. The location balloon 12 is at a distance from dilation balloon 18 such that location balloon 12 is at the bulbous urethra when the dilation balloon 18 is at the prostate urethra.

Balloons 18 and 12 are formed of a biocompatible material such as silicone elastomer, polyvinylchloride, polyester, natural or synthetic rubber, or polyurethane. The protuberance 19 may be made of the same material as the balloon 18 but is appreciably thicker and therefore stiffer than the remainder of the wall of the balloon. This thickness and stiffness enhances palpability. Alternatively, the protuberance may be made of a biocompatible material different from that of the balloon wall and be molded or bonded to the distal end of the balloon. In all cases the outer surface of the balloon should be smooth and when the material of the protuberance is different from that of the balloon wall such smoothness is achieved either by providing an outer sheath of a smooth material such as a silicone elastomer or by blending the outer surface of the protuberance into the outer surface of the balloon wall. Dilation balloon 18, including said integral protuberance, in general is made such that it does not expand beyond a predetermined diameter. Such limited expansion of the balloon 18 prevents overdilation and thus prevents damage to the prostate urethra during dilation. In one embodiment, the limited expansion is attained by making the dilation balloon of a non-distensible material such as polyvinylchloride, polyethylene terephthalate, or polyethylene. In the deflated state, such non-distensible balloon is in a folded configuration. Such limited expansion, alternatively, may be attained by making the balloon 18 of a limited distensible composite material as defined above. Multi-layer limited distensible materials of use in the present invention are described in U.S. Pat. No. 4,637,396 with respect to dilation "balloon 12" having a three layer wall. The inner layer is an elastic impervious polyurethane membrane, the middle layer is a knitted fabric tube, and the outer layer is an elastic impervious polyurethane or silicone membrane. An elastomeric outer layer or sheath made of silicone is particularly preferred because it increases patient comfort by providing a smooth outer surface for the deflated balloon. A particularly preferred embodiment comprises an outer layer of silicone and an inner layer of polyester.

Other multi-layer limited distensible materials of use in the present invention are the bistable materials described in U.S. Pat. No. 4,651,721, the disclosure of which is incorporated herein by reference. The limited distensible material may be part of a three layer composite having an outer layer which is elastic and may be formed of silicone elastomer, a middle layer of a bistable material such as polyester/polyurethane fabric, and an inner layer which is elastic and impervious and may be formed of silicone elastomer. The bistable material may be a fabric made of yarns composed of non-distensible fibers such as polyester fibers and distensible fibers such as polyurethane fibers. The distensible fibers allow for collapse of the balloon to about the outer diameter of the catheter tube 10', and the non-distensible fibers allow for inflation of the balloon to the predetermined diameter. If desired a suitable lubricant, for example fluorosilicone oil, may be placed between the layers, particularly the outer smooth silicone layer and its adjacent inner layer, to ensure smooth relative sliding motion of each layer with respect to the adjacent layer.

The predetermined diameter of the dilation balloon 18 is generally about 25 mm to about 40 mm.

The dilation balloon 18 has a proximal end 22, a distal end 24, and an integral protuberance 19 located at said distal end; and the location balloon 12 has a proximal end 26 and a distal end 28. The distance between the distal end 24 of the dilation balloon 18 and the proximal end 26 of the location balloon 12 varies with the relative location of the prostate urethra and the bulbous urethra in a patient, and is usually from about 1 cm to about 4 cm, most typically 1 cm. The device 10 has a proximal end 30 and a distal end 32. The proximal end 22 of the dilation balloon 18 is usually about 1 cm to about 3 cm from the proximal end 30 of the device 10. Optionally, the dilation balloon extends beyond the proximal end 30.

The length of the dilation balloon 18, that is the distance between the proximal end 22 and the distal end 24, depends upon the size of the prostate urethra of a patient. In general, such length of balloon 18 is about 3 cm to about 6 cm, commonly about 4 cm, in accordance with the general size of a male prostate urethra. The dilation balloon 18 may extend beyond the prostate urethra into the bladder neck, so allowing for some flexibility in use of a limited number of lengths of dilation balloons for different lengths of prostate urethras.

The length of the location balloon 12, that is the distance between the proximal end 26 and the distal end 28, is such that the balloon fits in the bulbous urethra of a patient. The balloon 12 need not occupy the entire space of the bulbous urethra. The functions of the balloon 12 are locating the prostate urethra, and fixating the device 10 against movement within the urethra, particularly against movement in the direction of the bladder. As a general rule, the length of the location balloon 12 is about 1 cm to 6 cm.

Radiopaque markers 27 and 29 are conveniently used to guide fluoroscopy examination.

FIG. 3 shows one embodiment of the dilation balloon 18 and integral protuberance 19 in inflated condition, as attached to catheter tube 10'. Drainage lumen 34 extends from the opening 31 at proximal end 30 through the catheter tube 10' to bladder drainage hole 36. The drainage lumen is an optional feature of device 10. A dilation lumen 38 communicates between a dilation balloon fill port 40 and the dilation balloon 18 through a dilation balloon opening 42. An inflation lumen 44 communicates between a location balloon fill port 46 and the location balloon 12 through a location balloon opening 48. Each of balloon fill ports 40 and 46 have a catheter valve or syringe fitting 50 and 52, respectively, to allow for connection of the fill ports with syringes for injection of fluid.

The invention will be more particularly described with reference to a preferred procedure for performing the method according to the invention.

After placing the patient in a lithotomy position, a Council catheter is passed into the bladder. If the bladder is empty, it is filled with approximately 100 ml. of sterile water or normal saline. A guide wire is passed through the Council catheter into the bladder and the catheter is then removed.

A device according to the invention is passed over the guide wire until both the dilation balloon and location balloon are in the bladder.

Before insertion, device 10 is in a completely deflated state such that balloons 18 and 12 are collapsed against the exterior of catheter tube 10'.

A filled 3 ml. syringe is attached to a two-way stopcock and this assembly is connected to the location balloon port 46. With a finger in the patient's rectum, the doctor palpates the apex of the prostate. The location balloon is inflated with approximately 1 ml. of contrast solution and the stopcock valve is closed.

The device is gently pulled until the location balloon is palpated at the apex of the prostate. If there is any resistance to this movement, the stopcock valve is opened and the location balloon is gradually deflated until it slides through to the apex.

The device is then withdrawn an additional 1.5 to 2 cm. until the protuberance 19 at the distal end 24 of the dilation balloon is palpated at the apex of the prostate. Centimeter markings 53[FIG. 2] may be provided on the catheter to facilitate the determination of its position. The said protuberance may be made from the same material as the outer wall of the dilation balloon or from a different material attached to said wall without disturbing the general smoothness of the outermost surface of the balloon.

Since the rectum is closer to the prostate urethra than it is to the bulbous urethra, palpation of the protuberance at the base of the dilation balloon when it is at the apex of the prostate should be easier than palpation of the location balloon in the bulbous urethra. However, it is to be understood that when the said protuberance is palpated at the apex of the prostate, the location balloon is in the bulbous urethra below the external sphincter. The location balloon is now inflated until resistance is met (approximately 1.3 ml. total volume) and the stopcock valve is then closed.

Conveniently, the location balloon 12 is inflated to at least some extent when it is in the vicinity of the bulbous urethra as determined by the doctor by rectal palpation. The location balloon 12 in inflated to its full extent after location at the bulbous urethra.

For inflation of the location balloon 12, the inflation lumen 44 leading to the location balloon 12 is connected to the said syringe inflating means, and inflation fluid is injected to inflate balloon 12 by fluid pressure. The inflation fluid is preferably a radiopaque fluid for post insertion X-ray examination and viewing of the device while in the body. Hypaque-25 and Renografin-60 are examples of suitable radiopaque fluids. Sufficient fluid is injected to secure the device 10 in its proper position. When the inflated location balloon 12 is properly located at the bulbous urethra distal from the external sphincter, the dilation balloon 18 is at its proper location at the prostate urethra since the location balloon 12 of device 10 is at a distance from the dilation balloon 18 such that when location balloon 12 is at the bulbous urethra then the dilation balloon 18 is at the prostate urethra. In this manner, dilation of the external sphincter, and possible harmful effects of such dilation, is avoided.

The dilation balloon 18 is connected to a pressure gauge through the dilation lumen 38, and dilation of the prostate is performed by inflation of the dilation balloon. Rectal palpation confirms proper positioning during dilation.

The proper inflation pressure for maximum dilation is attained by injecting a volume of fluid equal to the predetermined capacity of balloon 18, or by determining the maximum pressure on the pressure gauge when exerting pressure on the balloon 18. As is known in the dilation art in general, fluoroscopy aids in visualizing the extent of the balloon's expansion and in monitoring the dilation procedure.

In one preferred embodiment when the dilation balloon 18 is made of limited distensible material as described above, the balloon 18 expands to its predetermined maximum diameter.

After dilation, balloons 18 and 12 are deflated, and the device 10 is removed. Removal is facilitated with minimal distress to the patient when the dilation balloon is made of a multi-layer material, wherein the outer layer is silicone and the inner layer is, for example, a polyester. In such an embodiment the outer layer when deflated, because of its smooth and elastic character, bends over and folds in any wings and spikes in the deflated inner layer to provide a smooth outer surface of acceptable small diameter for easy withdrawal.

We claim:

1. An apparatus for dilation of the prostate urethra comprising:
   (i) an impervious urinary catheter for insertion in the prostate urethra, said catheter having proximal section and a distal section;
   (ii) a dilation balloon mounted on said proximal section of the catheter, said dilation balloon having a proximal end and a distal end wherein the distal end has an integral protuberance which makes the balloon wall at said distal end thicker and stiffer than the remainder of the balloon wall;
   (iii) a location balloon mounted on the catheter at a distance from the dilation balloon such that the location balloon is positioned at the bulbous urethra distal from the external sphincter to hold the catheter in place when the dilation balloon is positioned at the prostrate urethra; and
   (iv) activating means located at said distal section of the catheter for activating said dilation balloon and said location balloon.

2. An apparatus according to claim 1, wherein said dilation balloon is made from a multi-layer material.

3. An apparatus according to claim 2 wherein said multi-layer material comprises an outer layer of silicone and an inner layer of polyester.

4. An apparatus according to claim 2, wherein said multi-layer material comprises an inner and outer lyer of silicone and a middle layer of a limited distensible fabric.

5. An apparatus according to claim 2, wherein a lubricant is placed between the layers of the multi-layer material.

6. An apparatus according to claim 5, wherein said lubricant is a fluorosilicone oil.

7. An apparatus according to claim 1, wherein said catheter has three lumens extending from said proximal section, one lumen in communication with said dilation balloon, one lumen in communication with said location balloon, and one lumen adapted for communication with the bladder of a subject.

8. An apparatus according to claim 1, wherein said catheter has centimeter markings.

9. A method for the treatment of benign prostatic hyperplasia in a patient which comprises:
   inserting into the patient's prostate urethra a hollow, impervious, urinary catheter having a dilation balloon for dilating the prostate urethra and a location balloon for locating the dilation balloon at the prostate urethra, said dilation balloon having a proximal end and a distal end wherein the distal end has an integral protuberance which makes the balloon wall at said distal end thicker and stiffer than the remainder of the balloon wall, and said location balloon being axially mounted on said catheter at a distance from said dilation balloon such that the dilation balloon is positioned at the prostate urethra when the location balloon is positioned at the bulbous urethra distal from the external sphincter, and said location balloon on inflation being sized to fit in the bulbous urethra;
   placing said dilation balloon at the prostate urethra by palpating said protuberance at the apex of the prostate while locating and fixing said location balloon at the bulbous urethra;
   dilating said dilation balloon and thereby dilating the prostate urethra with said dilation balloon to alleviate obstruction of the prostate urethra resulting from benign prostatic hyperplasia;
   deflating said dilation balloon and location balloon; and removing said catheter from said prostate urethra.

10. A method according to claim 9, wherein after insertion of the catheter, the location balloon is inflated first before inflation of the dilation balloon.

11. A method according to claim 9, wherein liquid is circulated through said dilation balloon.

12. A method according to claim 9, wherein said dilation balloon is made from a multi-layer material.

13. A method according to claim 12, wherein said multi-layer material comprises an outer layer of silicone and an inner layer of polyester.

14. A method according to claim 12, wherein said multi-layer material comprises an inner and outer layer of silicone and a middle layer of a limited distensible fabric.

15. A method according to claim 12, wherein a lubricant is placed between the layers of the multi-layer material.

16. A method according to claim 15, wherein said lubricant is a fluorosilicone oil.

17. A method according to claim 9, wherein said catheter has centimeter markings.

* * * * *